(12) United States Patent
Mou et al.

(10) Patent No.: US 11,204,335 B2
(45) Date of Patent: Dec. 21, 2021

(54) ACTUATING AND SENSING MODULE

(71) Applicant: Microjet Technology Co., Ltd., Hsinchu (TW)

(72) Inventors: Hao-Jan Mou, Hsinchu (TW); Ta-Wei Hsueh, Hsinchu (TW); Ying-Lun Chang, Hsinchu (TW); Rong-Ho Yu, Hsinchu (TW); Cheng-Ming Chang, Hsinchu (TW); Hsien-Chung Tai, Hsinchu (TW); Wen-Hsiung Liao, Hsinchu (TW); Yung-Lung Han, Hsinchu (TW); Chi-Feng Huang, Hsinchu (TW)

(73) Assignee: MICROJET TECHNOLOGY CO., LTD., Hsinchu (TW)

( * ) Notice: Subject to any disclaimer, the term of this patent is extended or adjusted under 35 U.S.C. 154(b) by 665 days.

(21) Appl. No.: 16/012,207

(22) Filed: Jun. 19, 2018

(65) Prior Publication Data

US 2019/0011394 A1 Jan. 10, 2019

(30) Foreign Application Priority Data

Jul. 10, 2017 (TW) .................................. 106123109

(51) Int. Cl.
*G01N 27/407* (2006.01)
*G01D 21/02* (2006.01)
(Continued)

(52) U.S. Cl.
CPC ......... *G01N 27/4074* (2013.01); *G01D 21/02* (2013.01); *G01N 1/2273* (2013.01); *G01N 33/0047* (2013.01); *G01N 33/004* (2013.01)

(58) Field of Classification Search
CPC .......... G01N 27/4074; G01N 33/0047; G01N 1/2273; G01N 33/004; G01D 21/02
See application file for complete search history.

(56) References Cited

U.S. PATENT DOCUMENTS

| 6,354,185 B1 | 3/2002 | Sturman |
| 8,987,844 B2 | 3/2015 | Jenkins et al. |
(Continued)

FOREIGN PATENT DOCUMENTS

| CN | 101255861 A | 9/2008 |
| CN | 102679010 A | 9/2012 |
(Continued)

OTHER PUBLICATIONS

Extended European Search Report, dated Dec. 20, 2018, for European Application No. 18178579.1.
(Continued)

*Primary Examiner* — Dennis White
(74) *Attorney, Agent, or Firm* — Birch, Stewart, Kolasch & Birch, LLP

(57) ABSTRACT

An actuating and sensing module includes a substrate, at least one sensor and at least one actuating device. The at least one sensor is disposed on the substrate. The at least one actuating device is disposed on the substrate, and has at least one guiding channel between the actuating device and the substrate. The at least one guiding channel is disposed on one side of the at least one sensor. When the at least one actuating device is enabled, a fluid is transferred to the at least one sensor through the at least one guiding channel, so that the fluid is sensed by the at least one sensor.

19 Claims, 9 Drawing Sheets

(51) Int. Cl.
*G01N 33/00* (2006.01)
*G01N 1/22* (2006.01)

(56) References Cited

U.S. PATENT DOCUMENTS

| | | |
|---|---|---|
| 9,528,522 B2 | 12/2016 | Cummings |
| 2002/0043895 A1 | 4/2002 | Richards et al. |
| 2004/0202548 A1 | 10/2004 | Dai et al. |
| 2010/0229658 A1 | 9/2010 | Glezer et al. |
| 2014/0377099 A1* | 12/2014 | Hsueh ............... F04B 49/22 417/413.2 |
| 2015/0219608 A1* | 8/2015 | Choi ................. G06F 3/017 73/23.2 |
| 2016/0353186 A1* | 12/2016 | Rothkopf ............ H04R 1/028 |

FOREIGN PATENT DOCUMENTS

| | | |
|---|---|---|
| CN | 103808900 A | 5/2014 |
| CN | 204612745 U | 9/2015 |
| CN | 204988962 U | 1/2016 |
| CN | 205383064 U | 7/2016 |
| CN | 205458646 U | 8/2016 |
| CN | 205714691 U | 11/2016 |
| CN | 205744376 U | 11/2016 |
| CN | 206017108 U | 3/2017 |
| CN | 206129568 U | 4/2017 |
| CN | 206211877 U | 5/2017 |
| CN | 106908570 A | 6/2017 |
| CN | 206251549 U | 6/2017 |
| EP | 2733484 A1 | 5/2014 |
| EP | 2998582 A1 | 3/2016 |
| JP | 10-185929 A | 7/1998 |
| JP | 2005-24316 A | 1/2005 |
| JP | 2008-83043 A | 4/2008 |
| JP | 2009-526969 A | 7/2009 |
| TW | 370678 B | 9/1999 |
| TW | M525446 U | 7/2016 |
| TW | M544653 U | 7/2017 |
| WO | WO 2017/072489 A1 | 5/2017 |

OTHER PUBLICATIONS

Chinese Office Action and Search Report for Chinese Application No. 201710557671.1, dated Mar. 26, 2020.

Pourahmadi et al., "Variable-Flow Micro-Valve Structure Fabricated with Silicon Fusion Bonding," IEEE 4th Technical Digest on Solid-State Sensor and Actuator Workshop, Jun. 30, 1990, pp. 78-81.

Wang et al., "Research on Frequency Response Based on Piezoelectric Accelerometer," Journal Unknown, vol. 33, No. 9, 2014, pp. 116-119, with English abstract.

Indian Office Action, dated Jan. 12, 2021, for Indian Application No. 201824023054, with an English translation.

* cited by examiner

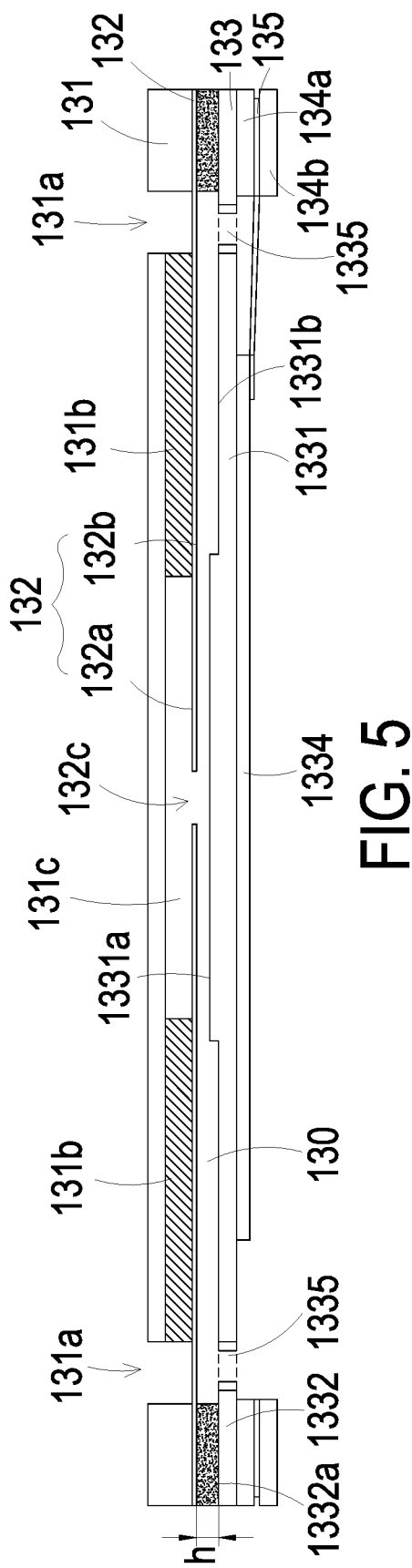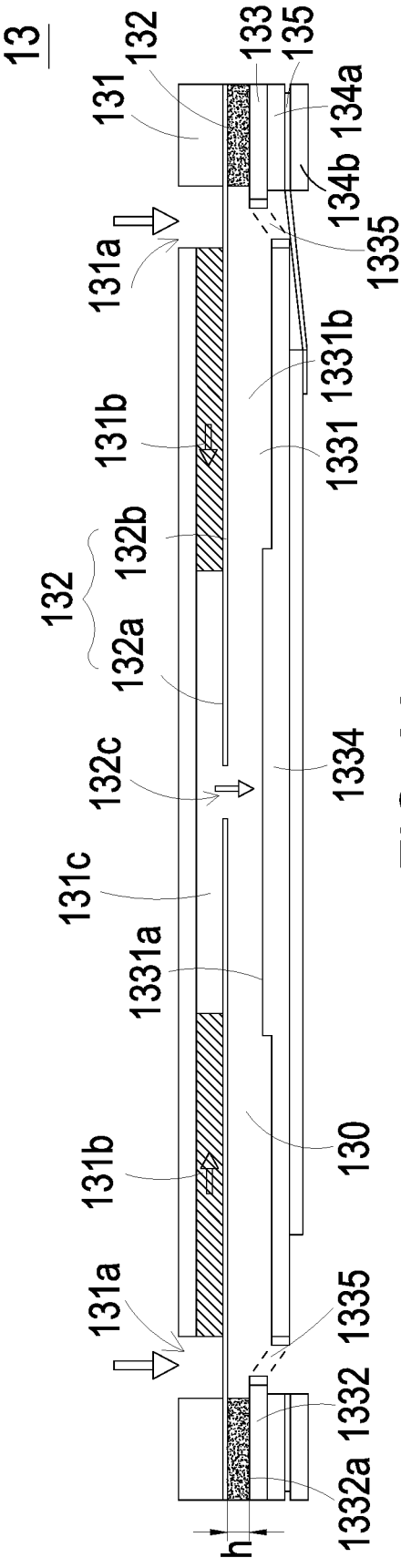

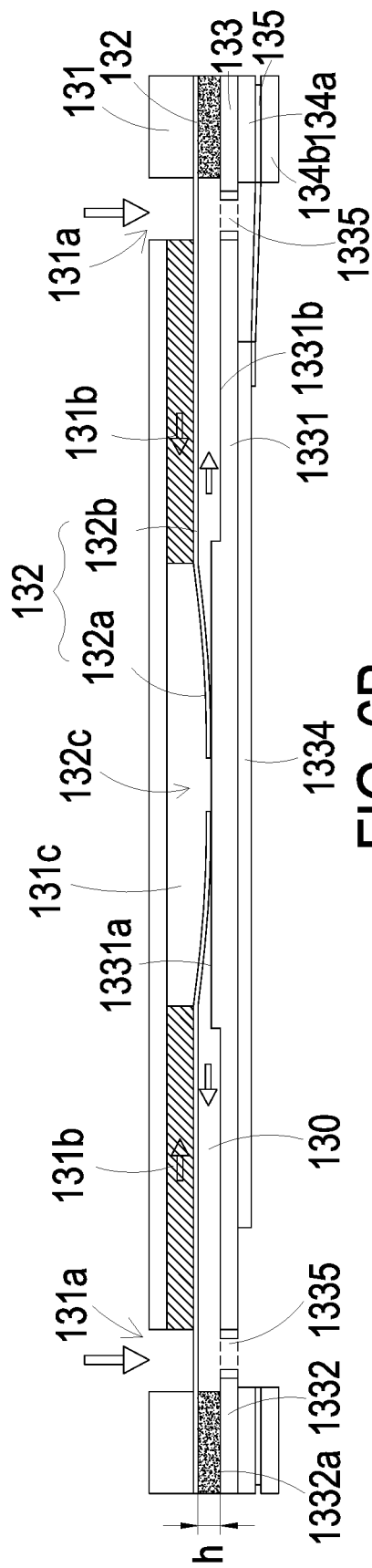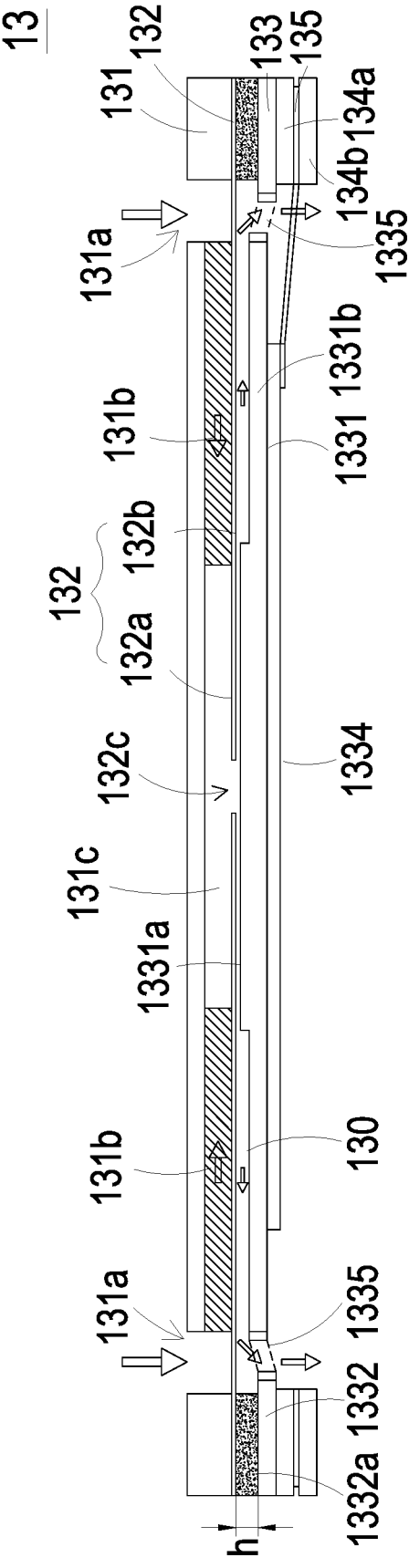

ACTUATING AND SENSING MODULE

FIELD OF THE INVENTION

The present disclosure relates to an actuating and sensing module, and more particularly to an actuating and sensing module for use in an electronic device to monitor the environment.

BACKGROUND OF THE INVENTION

Nowadays, people pay much attention to the devices and methods of monitoring the air quality in the environment. For example, it is important to monitor carbon monoxide, carbon dioxide, volatile organic compounds (VOC), PM2.5, and so on. The exposure of these gases in the environment will cause human health problems or even harm the life. Therefore, it is important for every country to develop and implement the environmental monitoring technology.

As known, portable electronic devices are widely used and applied in the modern lives. In addition, the portable electronic devices are indispensable electronic devices. Accordingly, it is feasible to use the portable electronic device to monitor the ambient air. If the portable electronic device is capable of immediately providing people with the monitored information in the environment for caution, it may help people escape or prevent from injuries and influence on human health caused by the gas exposure in the environment. In other words, the portable electronic device is suitably used for monitoring the ambient air in the environment.

Generally, the electronic device is additionally equipped with a sensor to monitor the environment and provide information about the environment to the user of the electronic device. However, the monitoring sensitivity and the precision of the sensor are usually not satisfied. For example, since the airflow is transferred to the sensor through natural convection, the amount of the airflow to be monitored by the sensor is neither stable nor uniform. Under this circumstance, the result of monitoring the environment is not accurate. Moreover, since the airflow is transferred to the sensor through natural convection, the response time of the sensor to monitor the environment is much longer. In other words, the real-time monitoring efficacy is low.

Therefore, there is a need of providing a technology of increasing the monitoring accuracy and reducing response time of the sensor.

SUMMARY OF THE INVENTION

An object of the present disclosure provides an actuating and sensing module. The actuating and sensing module is a modular structure of at least one sensor and at least one actuating device. The actuating device can increase the flowing speed and provide the amount of the fluid stably and uniformly. Since the sensor is provided with the amount of the fluid stably and uniformly, the time of the sensor in response to the fluid is largely reduced, thereby monitoring the fluid with precision.

In accordance with an aspect of the present disclosure, an actuating and sensing module is provided. The actuating and sensing module includes a substrate, at least one sensor and at least one actuating device. The at least one sensor is disposed on the substrate. The at least one actuating device is disposed on the substrate and has at least one guiding channel between the actuating device and the substrate, and is arranged on one side of the at least one sensor. When the at least one actuating device is enabled, a fluid is transferred to the at least one sensor through the at least one guiding channel, so that the fluid is sensed by the at least one sensor.

The above contents of the present disclosure will become more readily apparent to those ordinarily skilled in the art after reviewing the following detailed description and accompanying drawings, in which:

BRIEF DESCRIPTION OF THE DRAWINGS

FIG. 5 is a schematic cross-sectional view illustrating the fluid actuating device as shown in FIGS. 3A and 3B; and FIGS. 6A to 6E schematically illustrate the actions of the fluid actuating device of the actuating and sensing module according to the embodiment of the present disclosure.

DETAILED DESCRIPTION OF THE PREFERRED EMBODIMENT

The present disclosure will now be described more specifically with reference to the following embodiments. It is to be noted that the following descriptions of preferred embodiments of this invention are presented herein for purpose of illustration and description only. It is not intended to be exhaustive or to be limited to the precise form disclosed.

Figure 1A:
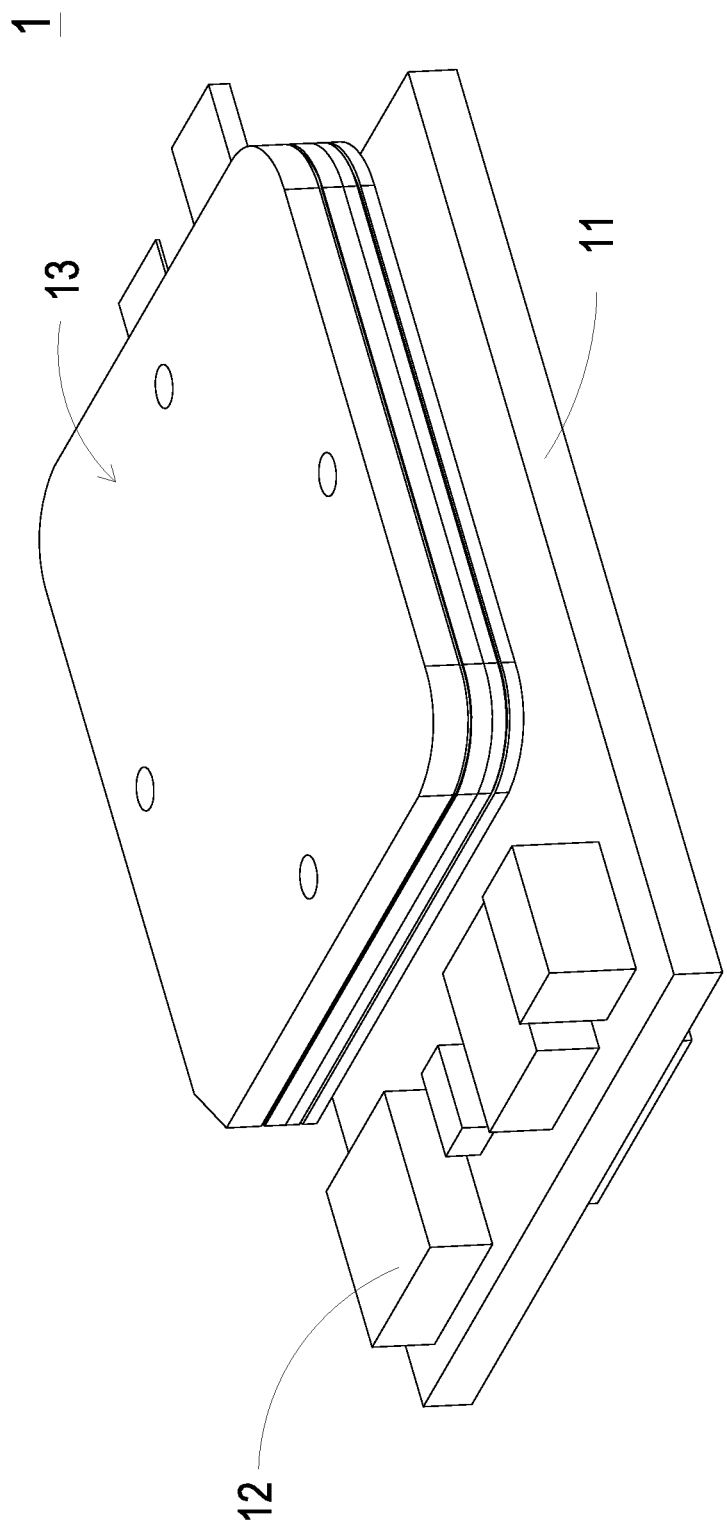
FIG. 1A is a schematic perspective view illustrating the structure of an actuating and sensing module according to an embodiment of the present disclosure.
Figure 1B:
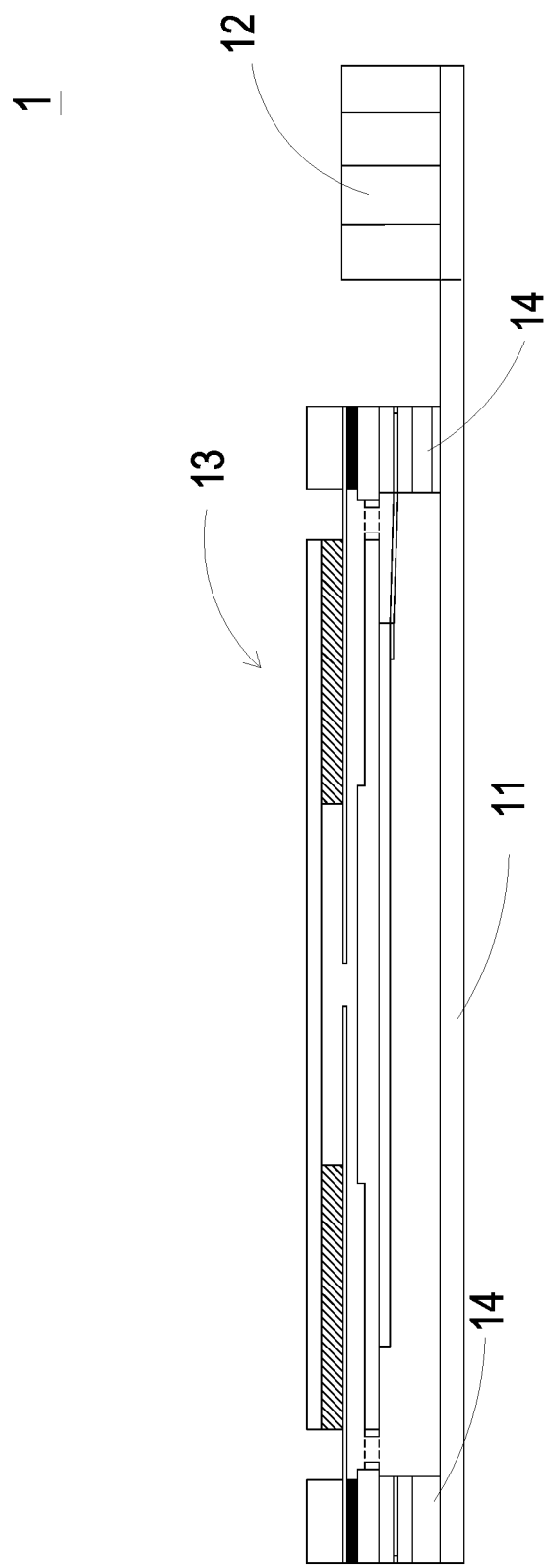
FIG. 1B is a schematic cross-sectional view illustrating the structure of the actuating and sensing module according to the embodiment of the present disclosure.
Figure 2:
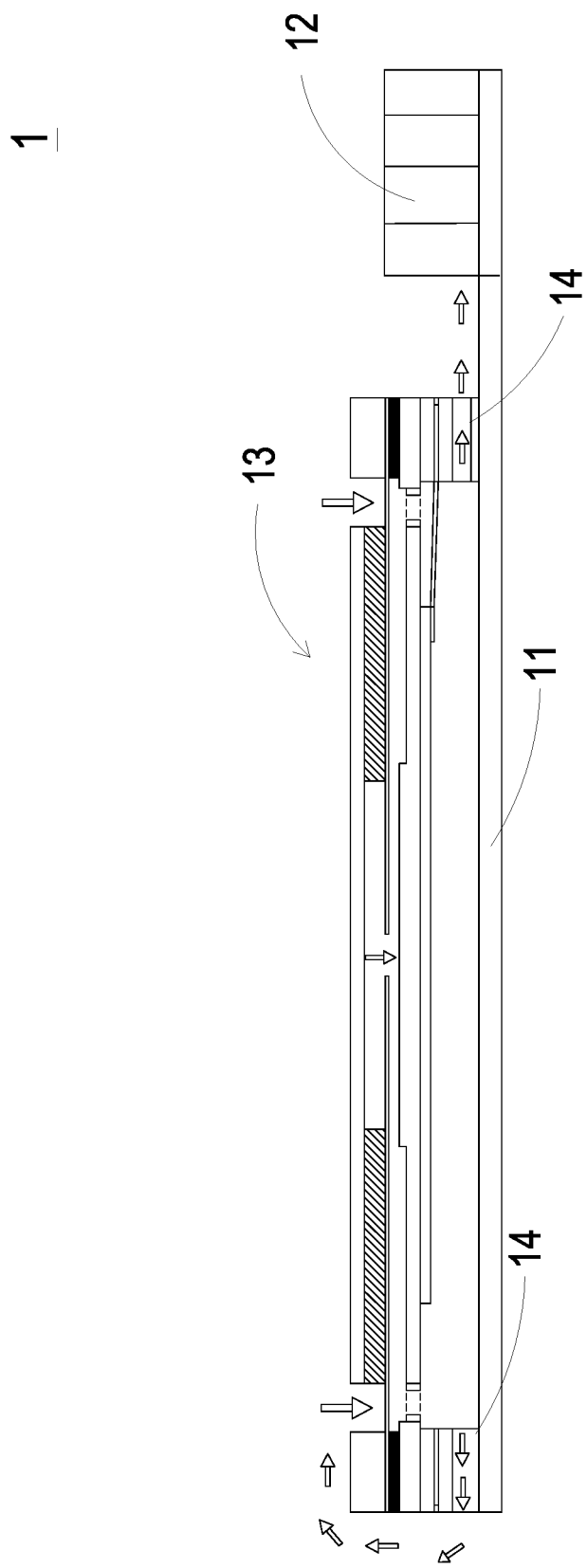
FIG. 2 is a schematic cross-sectional view illustrating the actions of the fluid actuating device of the actuating and sensing module according to the embodiment of the present disclosure.

Please refer to FIG. 1A, FIG. 1B and FIG. 2. The present discourse provides an actuating and sensing module 1 including at least one substrate 11, at least one sensor 12, at least one actuating device 13 and at least one guiding channel 14. When the actuating device 13 is enabled, at least one fluid is compressed. The number of the substrate 11, the sensor 12, the actuating device 13, the guiding channel 14 and the fluid is exemplified by one for each in the following embodiments but not limited thereto. It is noted that each of the substrate 11, the sensor 12, the actuating device 13, the guiding channel 14 and the fluid can also be provided in plural numbers.

FIG. 1A is a schematic perspective view illustrating the structure of an actuating and sensing module according to an embodiment of the present disclosure. FIG. 1B is a schematic cross-sectional view illustrating the structure of the actuating and sensing module according to the embodiment of the present disclosure. The actuating and sensing module 1 is applied to an electronic device for monitoring associated parameters in the environment. In an embodiment, the actuating and sensing module 1 includes a substrate 11, at least one sensor 12 and at least one actuating device 13. The at least one sensor 12 and the at least one actuating device 13 are integrated as the actuating and sensing module 1. The actuating device 13 is disposed on one side of the sensor 12. The actuating device 13 includes at least one guiding channel 14. After the actuating device 13 is enabled, fluid is driven to be transferred through the at least one guiding channel 14. When the fluid is transferred to the sensor 12, the fluid is sensed by the sensor 12.

The actuating device 13 is a driving device capable of driving a desired system in response to a control signal. An example of the actuating device 13 includes but is not limited to an electric actuating device, a magnetic actuating device, a thermal actuating device, a piezoelectric actuating device, and a fluid actuating device. For example, the electric actuating device is an electric actuating device of a DC motor, an AC motor or a step motor, the magnetic actuating device is an magnetic actuating device of a magnetic coil motor, the thermal actuating device is a thermal actuating device of a heat pump, the piezoelectric actuating device is a piezoelectric actuating device of a piezoelectric pump, and the fluid actuating device is a fluid actuating device of a gas pump or a liquid pump.

An example of the sensor 12 includes but is not limited to a temperature sensor, a volatile organic compound sensor (e.g., a sensor for measuring formaldehyde or ammonia gas), a particulate sensor (e.g., a PM2.5 particle sensor), a carbon monoxide sensor, a carbon dioxide sensor, an oxygen sensor, an ozone sensor, any other appropriate gas sensor, a humidity sensor, a water content sensor, a substance sensor (e.g., a sensor for measuring compounds or biological substances in liquid or air), a water quality sensor, any other appropriate liquid sensor, a light sensor, or the combination thereof.

Please refer to FIGS. 1A and 1B. For illustration, the actuating device 13 of the actuating and sensing module 1 is a fluid actuating device. The actions of the fluid actuating device will be described as follows. As shown in FIG. 1A, the substrate 11 is a platform for integrating the sensor 12 with the fluid actuating device 13. For example, the substrate 11 is a printed circuit board (PCB). An array of the sensor 12 and the fluid actuating device 13 is installed on the substrate 11. The fluid actuating device 13 is a driving structure of a piezoelectric pump or a driving structure of a micro-electro-mechanical system (MEMS) pump.

Hereinafter, the actions of the fluid actuating device 13 of a piezoelectric pump will be described as follows.

Figure 3A:
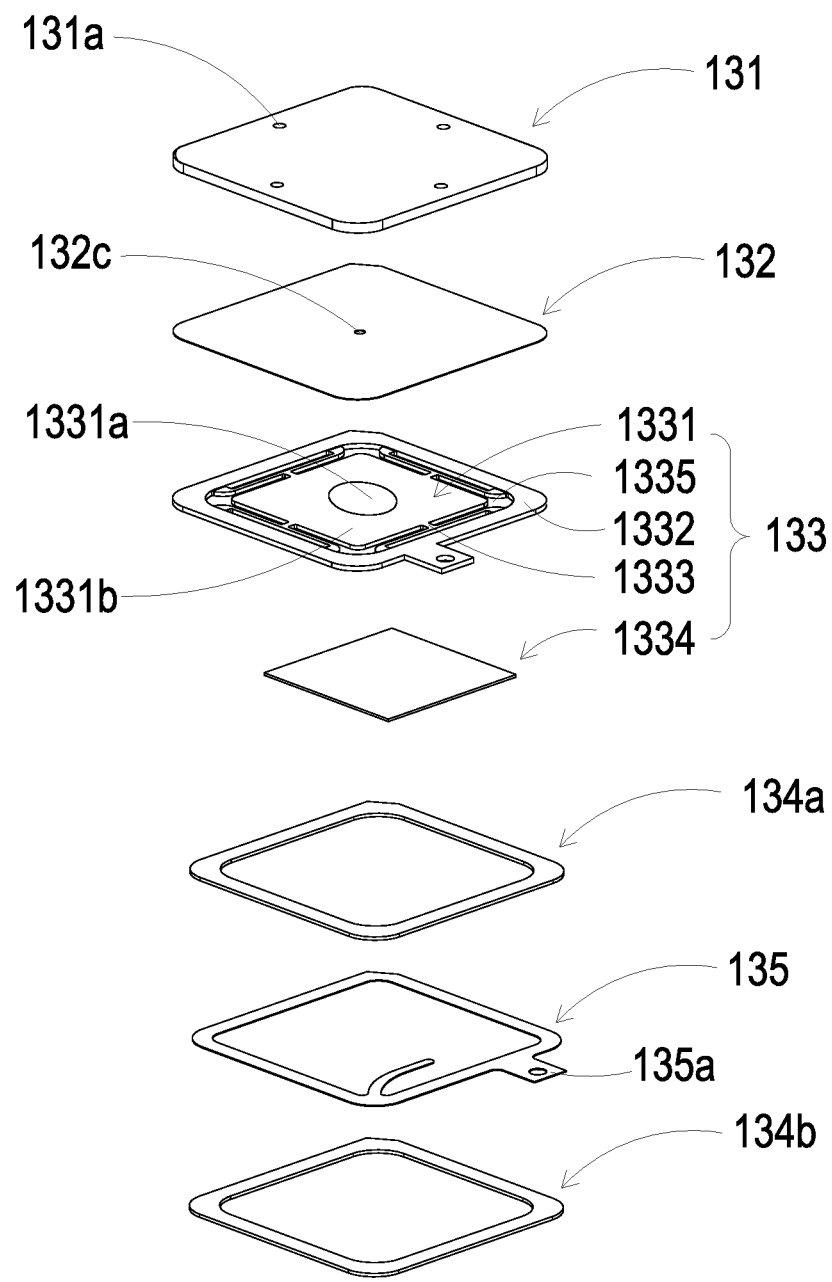
FIG. 3A is a schematic exploded view illustrating a fluid actuating device used in the actuating and sensing module of the present disclosure.
Figure 3B:
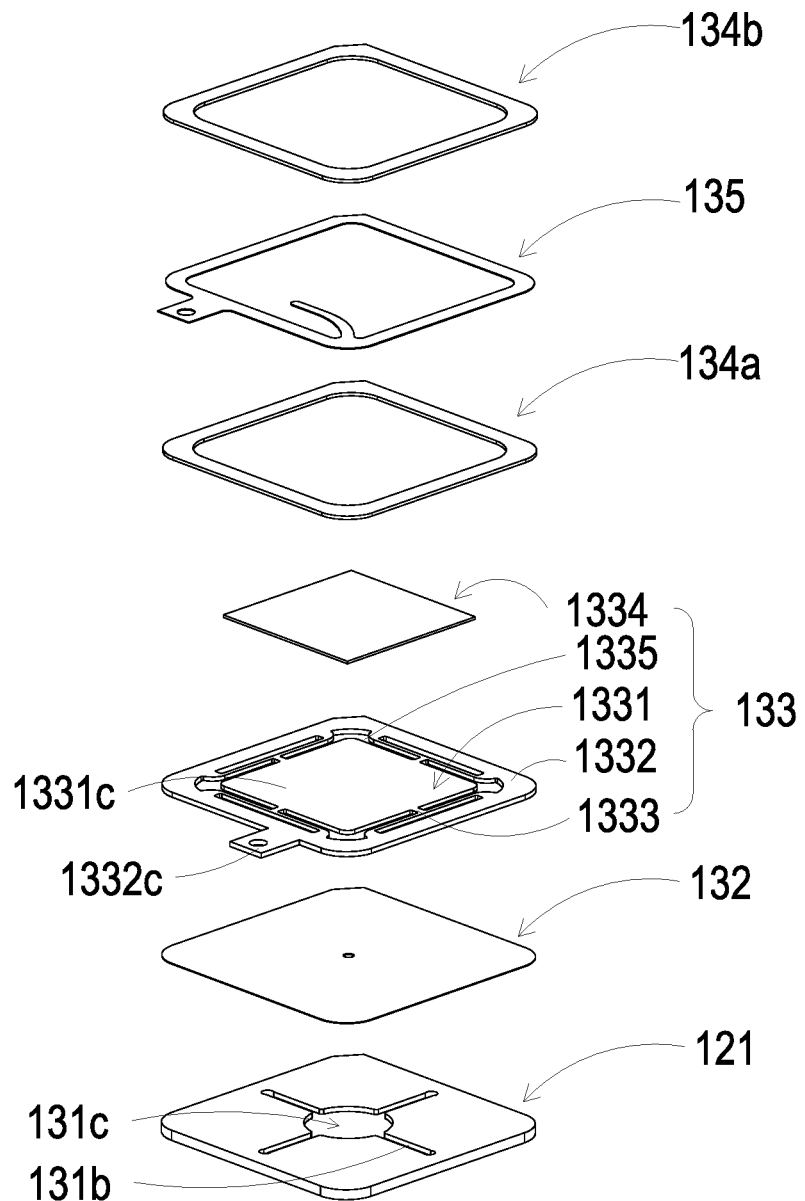
FIG. 3B is a schematic exploded view illustrating the fluid actuating device of FIG. 3A and taken along another viewpoint.

Please refer to FIG. 3A and FIG. 3B. The fluid actuating device 13 includes a fluid inlet plate 131, a resonance plate 132, a piezoelectric actuator 133, a first insulation plate 134a, a conducting plate 135 and a second insulation plate 134b. The piezoelectric actuator 133 is aligned with the resonance plate 132. The fluid inlet plate 131, the resonance plate 132, the piezoelectric actuator 133, the first insulation plate 134a, the conducting plate 135 and the second insulation plate 134b are stacked on each other sequentially. After the above components are combined together, the cross-sectional view of the resulting structure of the fluid actuating device 13 is shown in FIG. 5.

The fluid inlet plate 131 includes at least one inlet 131a. Preferably but not exclusively, the fluid inlet plate 131 includes four inlets 131a. The inlets 131a run through the fluid inlet plate 131. In response to the action of the atmospheric pressure, the fluid can be introduced into the fluid actuating device 13 through the at least one inlet 131a. Moreover, at least one convergence channel 131b is formed on a first surface of the fluid inlet plate 131, and is in communication with the at least one inlet 131a on a second surface of the fluid inlet plate 131. Moreover, a central cavity 131c is located at the intersection of the convergence channels 131b. The central cavity 131c is in communication with the at least one convergence channel 131b, such that the fluid from the at least one inlet 131a would be introduced into the at least one convergence channel 131b and is guided to the central cavity 131c. Consequently, the fluid can be transferred by the fluid actuating device 13. In this embodiment, the at least one inlet 131a, the at least one convergence channel 131b and the central cavity 131c of the fluid inlet plate 131 are integrally formed. The central cavity 131c is a convergence chamber for temporarily storing the fluid. In some embodiments, the fluid inlet plate 131 may be, for example made of stainless steel. In another embodiment, the depth of the convergence chamber defined by the central cavity 131c is equal to the depth of the at least one convergence channel 131b. The resonance plate 132 may be made of, but not limited to a flexible material. The resonance plate 132 includes a central aperture 132c disposed corresponding to the central cavity 131c of the fluid inlet plate 131. Consequently, the fluid can be transferred through the central aperture 132c. In other embodiments, the resonance plate 132 may be made of, but not limited to a copper material.

The piezoelectric actuator 133 includes a suspension plate 1331, an outer frame 1332, at least one bracket 1333 and a piezoelectric plate 1334. The piezoelectric plate 1334 is attached on a first surface 1331c of the suspension plate 1331. In response to an applied voltage, the piezoelectric plate 1334 would be subjected to a deformation. When the piezoelectric plate 1334 is subjected to the deformation, it facilitates a bending vibration of the suspension plate 1331. The at least one bracket 1333 is connected between the suspension plate 1331 and the outer frame 1332, while the two ends of the bracket 1333 are connected with the outer frame 1332 and the suspension plate 1331 respectively that the bracket 1333 can elastically support the suspension plate 1331. At least one vacant space 1335 is formed between the bracket 1333, the suspension plate 1331 and the outer frame 1332. The at least one vacant space 1335 is in communication with the fluid guiding channel for allowing the fluid to go through. The type of the suspension plate 1331 and the outer frame 1332 and the type and the number of the at least one bracket 1333 may be varied according to the practical requirements. The outer frame 1332 is arranged around the suspension plate 1331. Moreover, a conducting pin 1332c is protruded outwardly from the outer frame 1332 so as to be electrically connected with an external circuit (not shown).

Figure 4:
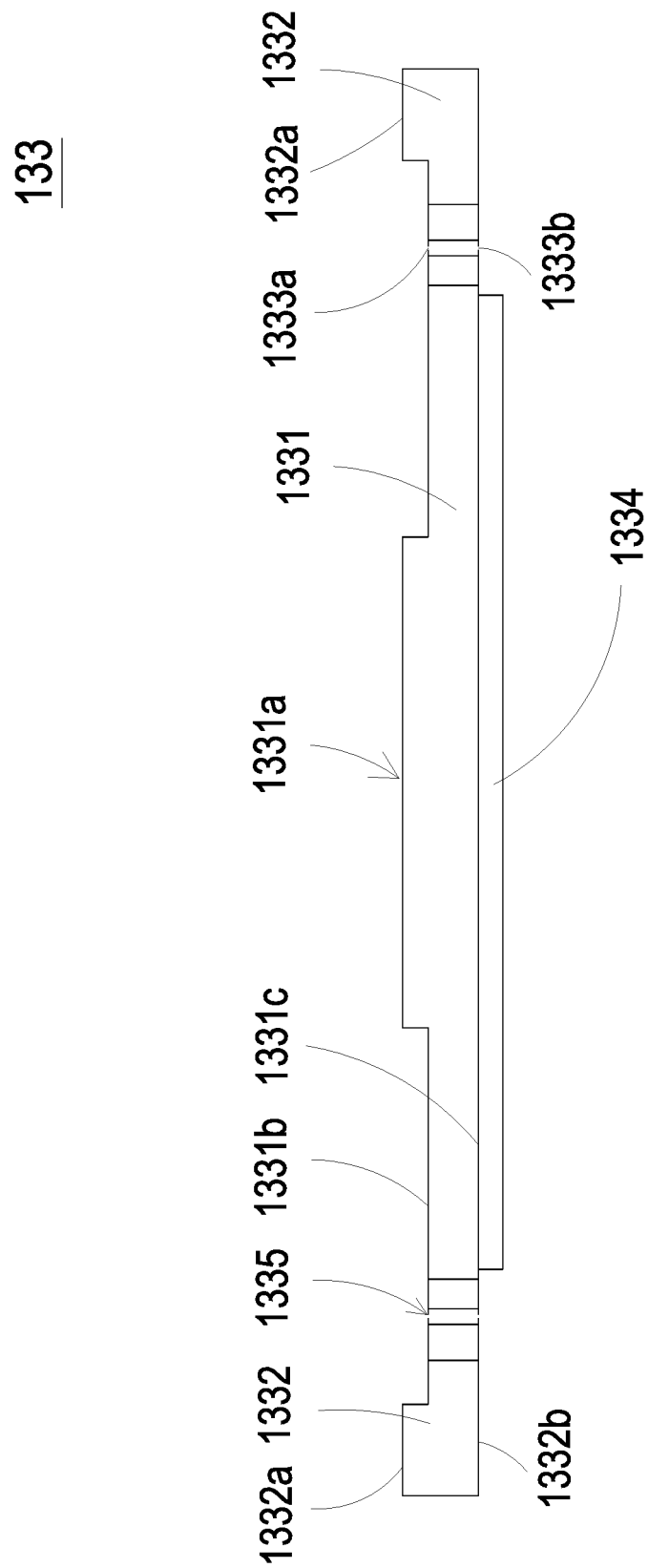
FIG. 4 is a schematic cross-sectional view illustrating the piezoelectric actuator of the fluid actuating device as shown in FIGS. 3A and 3B.

As shown in FIG. 4, the suspension plate 1331 has a bulge 1331a that makes the suspension plate 1331 a stepped structure. The bulge 1331a is formed on a second surface 1331b of the suspension plate 1331. The bulge 1331a may be a circular convex structure. A top surface of the bulge 1331a of the suspension plate 1331 is coplanar with a second surface 1332a of the outer frame 1332, while the second surface 1331b of the suspension plate 1331 is coplanar with a second surface 1333a of the bracket 1333. Moreover, there is a specific depth from the bulge 1331a of the suspension plate 1331 (or the second surface 1332a of the outer frame 1332) to the second surface 1331b of the suspension plate 1331 (or the second surface 1333a of the bracket 1333). A first surface 1331c of the suspension plate 1331, a first surface 1332b of the outer frame 1332 and a first surface 1333b of the bracket 1333 are coplanar with each other. The piezoelectric plate 1334 is attached on the first surface 1331c of the suspension plate 1331. In some other embodiments, the suspension plate 1331 may be a square plate structure with two flat surfaces, but the type of the suspension plate 1331 may be varied according to the practical requirements. In this embodiment, the suspension plate 1331, the at least bracket 1333 and the outer frame 1332 may be integrally formed from a metal plate (e.g., a stainless steel plate). In an embodiment, the length of a side of the piezoelectric plate 1334 is smaller than the length of a side of the suspension plate 1331. In another embodiment, the length of a side of the piezoelectric plate 1334 is equal to the length of a side of the suspension plate 1331. Similarly, the piezoelectric plate 1334 is a square plate structure corresponding to the suspension plate 1331 in terms of the design.

In this embodiment, the first insulation plate 134a, the conducting plate 135 and the second insulation plate 134b of the fluid actuating device 13 are stacked on each other sequentially and located under the piezoelectric actuator 133. The profiles of the first insulation plate 134a, the conducting plate 135 and the second insulation plate 134b substantially match the profile of the outer frame 1332 of the piezoelectric actuator 133, as shown in FIG. 3A. In some embodiments, the first insulation plate 134a and the second insulation plate 134b may be made of an insulating material (e.g. a plastic material) for providing insulating efficacy. In other embodiments, the conducting plate 135 may be made of an electrically conductive material (e.g. a metallic material) for providing electrically conducting efficacy. In this embodiment, the conducting plate 135 may have a conducting pin 135a disposed thereon so as to be electrically connected with an external circuit (not shown).

Please refer to FIG. 5. In an embodiment, the fluid inlet plate 131, the resonance plate 132, the piezoelectric actuator 133, the first insulation plate 134a, the conducting plate 135 and the second insulation plate 134b of the fluid actuating device 13 are stacked on each other sequentially. Moreover, there is a gap h between the resonance plate 132 and the outer frame 1332 of the piezoelectric actuator 133. In this embodiment, the gap h between the resonance plate 132 and the outer frame 1332 of the piezoelectric actuator 133, may be filled with a filler (e.g., a conductive adhesive) so that a depth from the resonance plate 132 to the bulge 1331a of the suspension plate 1331 of the piezoelectric actuator 133 can be maintained. The gap h ensures the proper distance between the resonance plate 132 and the bulge 1331a of the suspension plate 1331 of the piezoelectric actuator 133, so that the fluid can be transferred quickly, the contact interference is reduced and the generated noise is largely reduced. In some embodiments, alternatively, the height of the outer frame 1332 of the piezoelectric actuator 133 is increased, so that a gap is formed between the resonance plate 132 and the piezoelectric actuator 133.

Please refer to FIG. 3A, FIG. 3B and FIG. 5. After the fluid inlet plate 131, the resonance plate 132 and the piezoelectric actuator 133 are combined together, a movable part 132a and a fixed part 132b of the resonance plate 132 are defined. A convergence chamber for converging the fluid is defined by the movable part 132a of the resonance plate 132 and the fluid inlet plate 131 collaboratively. Moreover, a first chamber 130 is formed between the resonance plate 132 and the piezoelectric actuator 133 for temporarily storing the fluid. Through the central aperture 132c of the resonance plate 132, the first chamber 130 is in communication with the central cavity 131c of the fluid inlet plate 131. The peripheral regions of the first chamber 130 are in communication with the guiding channel 14 through the vacant space 1335 between the brackets 1333 of the piezoelectric actuator 133.

Figure 6D:
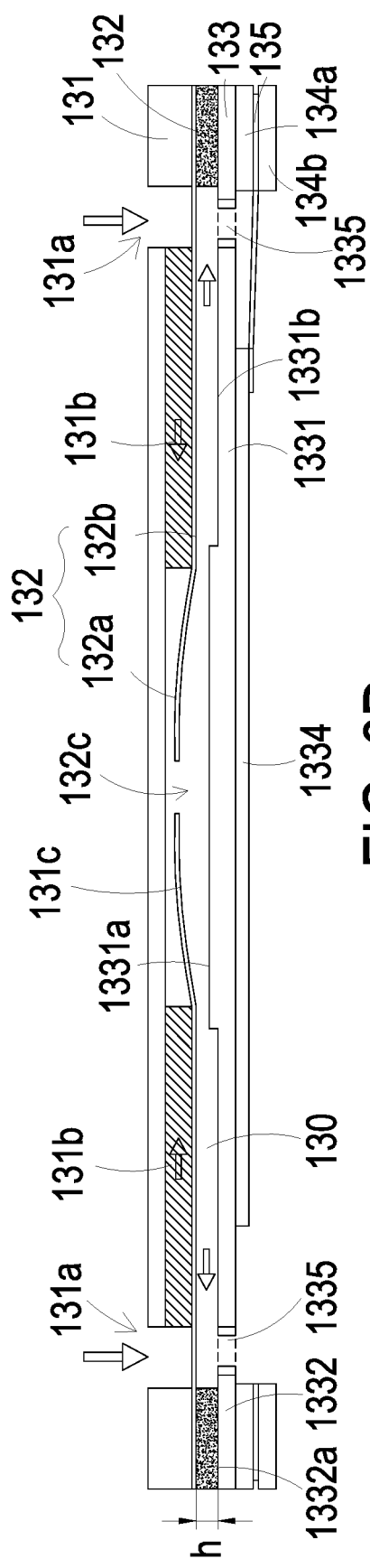
Figure 6E:
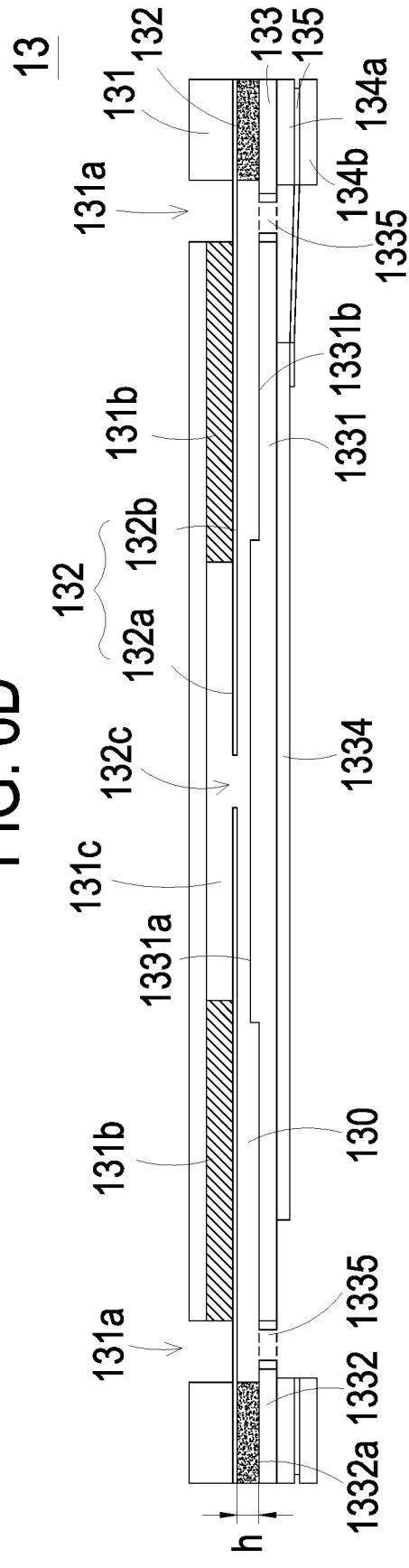

FIGS. 6A to 6E schematically illustrate the actions of the fluid actuating device of the actuating and sensing module according to the embodiment of the present disclosure. Please refer to FIG. 3A, FIG. 3B, FIG. 5 and FIGS. 6A to 6E. The actions of the fluid actuating device will be described as follows. When the fluid actuating device 13 is enabled, the piezoelectric actuator 133 vibrates along a vertical direction in a reciprocating manner by using the bracket 1333 as a fulcrum. Please refer to FIG. 6A. Since the resonance plate 132 is light and thin, the resonance plate 132 vibrates along the vertical direction in the reciprocating manner because of the resonance of the piezoelectric actuator 133 in response to the applied voltage. Besides, a region of the resonance plate 132 spatially corresponding to the central cavity 131c of the fluid inlet plate 131 is also subjected to a bending deformation. The region of the resonance plate 132 corresponding to the central cavity 131c of the fluid inlet plate 131 is the movable part 132a of the resonance plate 132. More specifically, when the piezoelectric actuator 133 vibrates downwardly, the movable part 132a of the resonance plate 132 is subjected to the bending deformation because the movable part 132a of the resonance plate 132 is pushed by the fluid and vibrates in response to the piezoelectric actuator 133. In response to the downward vibration of the piezoelectric actuator 133, the fluid is fed into the at least one inlet 131a of the fluid inlet plate 131. Then, the fluid is transferred to the central cavity 131c of the fluid inlet plate 131 through the at least one convergence channel 131b. Then, the fluid is transferred through the central aperture 132c of the resonance plate 132 spatially corresponding to the central cavity 131c, and introduced downwardly into the first chamber 130. As the piezoelectric actuator 133 is enabled, the resonance of the resonance plate 132 occurs. Consequently, the resonance plate 132 vibrates along the vertical direction in the reciprocating manner. As shown in FIG. 6B, during the vibration of the resonance plate 132 at this stage, the movable part 132a of the resonance plate 132 moves down to contact and attach on the bulge 1331a of the suspension plate 1331 of the piezoelectric actuator 133, and a distance from the fixed part 132b of the resonance plate 132 to a region of the suspension plate 1331 except the bulge 1331a remains the same. Owing to the deformation of the resonance plate 132 described above, a middle communication space of the first chamber 130 is closed and the volume of the first chamber 130 is compressed. The pressure gradient occurs to push the fluid in the first chamber 130 moving toward peripheral regions of the first chamber 130, and flowing downwardly through the vacant space 1335 of the piezoelectric actuator 133. Referring to FIG. 6C, the movable part 132a of the resonance plate 132 returns to its original position when the piezoelectric actuator 133 vibrates upwardly. Consequently, the volume of the first chamber 130 is continuously compressed to generate the pressure gradient which makes the fluid in the first chamber 130 continuously pushed toward peripheral regions. Meanwhile, the fluid is continuously fed into the at least one inlet 131a of the fluid inlet plate 131, and transferred to the central cavity 131c. Then, as shown in FIG. 6D, the resonance plate 132 moves upwardly, which is cause by the resonance of the upward motion of the piezoelectric actuator 133. That is, the movable part 132a of the resonance plate 132 is also vibrated upwardly. Consequently, it decreases the current of the fluid from the at least one inlet 131a of the fluid inlet plate 131 into the central cavity 131c. At last, as shown in FIG. 6E, the movable part 132a of the resonance plate 132 has returned to its original position. As the embodiments described above, when the resonance plate 132 vibrates along the vertical direction in the reciprocating manner, the gap h between the resonance plate 132 and the piezoelectric actuator 133 is helpful to increase the maximum displacement along the vertical direction during the vibration. In other words, the configuration of the gap h between the resonance plate 132 and the piezoelectric actuator 133 can increase the amplitude of vibration of the resonance plate 132. Consequently, a pressure gradient is generated in the fluid guiding channels of the fluid actuating device 13 to facilitate the fluid to flow at a high speed. Moreover, since there is an impedance difference between the feeding direction and the exiting direction, the fluid can be transmitted from the inlet side to the outlet side. Moreover, even if the outlet side has a gas pressure, the fluid actuating device 13 still has the capability of pushing the fluid to the guiding channel 14 while achieving the silent efficacy. The steps of FIGS. 6A to 6E may be done repeatedly. Consequently, the ambient fluid is transferred by the fluid actuating device 13 from the outside to the inside.

Please refer to FIG. 2 again. After the fluid inlet plate 131, the resonance plate 132, the piezoelectric actuator 133, the first insulation plate 134a, the conducting plate 135 and the second insulation plate 134b are stacked on each other sequentially, the fluid actuating device 13 is assembled. After the fluid actuating device 13 is installed on the substrate 11, the at least one guiding channel 14 is arranged between the fluid actuating device 13 and the substrate 11. The guiding channel 14 is disposed on one side of the sensor 12. When the fluid actuating device 13 is enabled to compress the fluid, the fluid is transferred through the guiding channel 14 to flow toward the sensor 12 along the direction indicated by the arrow (see FIG. 2). Consequently, the fluid is sensed by the sensor 12. Since the fluid is guided to the sensor 12 by the fluid actuating device 13, which provides the sensor 12 with the amount of the fluid stably and uniformly, the time of the sensor in response to the fluid is largely reduced, thereby monitoring the fluid with precision. In other words, the technology of the present disclosure is industrially valuable.

From the above descriptions, the present disclosure provides an actuating and sensing module. The actuating and sensing module is a modular structure of at least one sensor and at least one actuating device. The actuating device can increase the flowing speed and provide the amount of the fluid stably and uniformly. Since the sensor is provided with the amount of the fluid stably and uniformly, the time of the sensor in response to the fluid is largely reduced, thereby monitoring the fluid with precision.

While the invention has been described in terms of what is presently considered to be the most practical and preferred embodiments, it is to be understood that the invention needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. An actuating and sensing module, comprising:
    a substrate;
    at least one sensor disposed on the substrate; and
    at least one actuating device disposed on the substrate and having at least one guiding channel between the actuating device and the substrate, wherein the guiding channel is disposed on one side of the sensor, wherein the actuating device has at least one inlet and a central cavity defining a convergence chamber, and the guiding channel has at least one outlet disposed corresponding to the sensor, wherein when the actuating device is enabled, a fluid is compressed to flow and is converged to the central cavity from the at least one inlet and transferred to the sensor through the at least one outlet of the guiding channel, so that the compressed fluid is sensed by the sensor.

2. The actuating and sensing module according to claim 1, wherein the fluid is a gas.

3. The actuating and sensing module according to claim 1, wherein the fluid is a liquid.

4. The actuating and sensing module according to claim 1, wherein the substrate is a printed circuit board, and an array of the at least one sensor and the at least one actuating device is installed on the substrate.

5. The actuating and sensing module according to claim 1, wherein the sensor comprises at least one selected from the group consisting of an oxygen sensor, a carbon monoxide sensor and a carbon dioxide sensor.

6. The actuating and sensing module according to claim 1, wherein the sensor comprises a liquid sensor.

7. The actuating and sensing module according to claim 1, wherein the sensor comprises at least one selected from the group consisting of a temperature sensor, a liquid sensor and a humidity sensor.

8. The actuating and sensing module according to claim 1, wherein the sensor comprises an ozone sensor.

9. The actuating and sensing module according to claim 1, wherein the sensor comprises a particulate sensor.

10. The actuating and sensing module according to claim 1, wherein the sensor comprises a volatile organic compound sensor.

11. The actuating and sensing module according to claim 1, wherein the sensor comprises a light sensor.

12. The actuating and sensing module according to claim 1, wherein the actuating device is a fluid actuating device.

13. The actuating and sensing module according to claim 12, wherein the fluid actuating device is a micro-electro-mechanical system (MEMS) pump.

14. The actuating and sensing module according to claim 12, wherein the fluid actuating device is a piezoelectric pump.

15. The actuating and sensing module according to claim 14, wherein the fluid actuating device comprises:
    a fluid inlet plate having the at least one inlet, at least one convergence channel and the central cavity defining the convergence chamber, wherein the at least one inlet allows the fluid to flow in, and at least one convergence channel is disposed corresponding to the at least one inlet, and guides the fluid from the at least one inlet toward the convergence chamber defined by the central cavity;
    a resonance plate having a central aperture and a movable part, wherein the central aperture is aligned with the convergence chamber and the movable part surrounds the central aperture; and
    a piezoelectric actuator aligned with the resonance plate, wherein a gap is formed between the resonance plate and the piezoelectric actuator to define a first chamber, so that the fluid from the at least one inlet of the fluid inlet plate is converged to the central cavity along the at least one convergence channel and flows into the first chamber through the central aperture of the resonance plate when the piezoelectric actuator is enabled, whereby the fluid is further transferred through a resonance between the piezoelectric actuator and the movable part of the resonance plate.

16. The actuating and sensing module according to claim 15, wherein the piezoelectric actuator comprises:

a suspension plate having a first surface and an opposing second surface, wherein the suspension plate is permitted to undergo a bending vibration;
an outer frame arranged around the suspension plate;
at least one bracket connected between the suspension plate and the outer frame for elastically supporting the suspension plate; and
a piezoelectric plate, wherein a length of a side of the piezoelectric plate is smaller than or equal to a length of a side of the suspension plate, and the piezoelectric plate is attached on the first surface of the suspension plate, wherein when a voltage is applied to the piezoelectric plate, the suspension plate is driven to undergo the bending vibration.

17. The actuating and sensing module according to claim 16, wherein the suspension plate is a square suspension plate with a bulge.

18. The actuating and sensing module according to claim 15, wherein the fluid actuating device further comprises a conducting plate, a first insulation plate and a second insulation plate, wherein the fluid inlet plate, the resonance plate, the piezoelectric actuator, the first insulation plate, the conducting plate and the second insulation plate are stacked on each other sequentially.

19. An actuating and sensing module, comprising:
at least one actuating device disposed on the substrate and having at least one guiding channel between the actuating device and the substrate, wherein the guiding channel is disposed on one side of the sensor, wherein the actuating device has at least one inlet and a central cavity defining a convergence chamber, and the guiding channel has at least one outlet disposed corresponding to the sensor, wherein when the actuating device is enabled, at least one fluid is compressed to flow and is converged to the central cavity from the at least one inlet and transferred to the sensor through the at least one outlet of the guiding channel, so that the compressed fluid is sensed by the sensor.

* * * * *